(12) United States Patent
Polenz et al.

(10) Patent No.: US 10,500,558 B2
(45) Date of Patent: Dec. 10, 2019

(54) REFLECTING SPHERICAL MICROCAPSULES AND METHODS OF THEIR PRODUCTION

(71) Applicant: Max-Planck-Gesellschaft zur Foerderung der Wissenschaften e.V., Munich (DE)

(72) Inventors: Ingmar Polenz, Matrei im Osttirol (AT); Huixuan Wu, Lawrence, KS (US); Jean-Christophe Baret, Cestas (FR); Eberhard Bodenschatz, Goettingen (DE)

(73) Assignee: MAX-PLANCK-GESELLSCHAFT ZUR FOERDERUNG DER WISSENSCHAFTEN E.V., Munich (DE)

(*) Notice: Subject to any disclaimer, the term of this patent is extended or adjusted under 35 U.S.C. 154(b) by 0 days.

(21) Appl. No.: 15/497,603

(22) Filed: Apr. 26, 2017

(65) Prior Publication Data

US 2017/0225142 A1  Aug. 10, 2017

Related U.S. Application Data

(63) Continuation of application No. PCT/EP2015/075441, filed on Nov. 2, 2015.

(30) Foreign Application Priority Data

Nov. 1, 2014 (EP) .................................... 14191390

(51) Int. Cl.
*B01J 13/16* (2006.01)
*C08K 9/02* (2006.01)
(Continued)

(52) U.S. Cl.
CPC .......... *B01J 13/16* (2013.01); *C08G 18/6423* (2013.01); *C08G 18/7621* (2013.01); *C08K 3/22* (2013.01);
(Continued)

(58) Field of Classification Search
None
See application file for complete search history.

(56) References Cited

U.S. PATENT DOCUMENTS

| | | | |
|---|---|---|---|
| 5,298,258 | A | 3/1994 | Akemi |
| 2012/0003285 | A1 | 1/2012 | Bibette |
| 2012/0129742 | A1 | 5/2012 | Matray |

FOREIGN PATENT DOCUMENTS

| | | | | |
|---|---|---|---|---|
| EP | 0 484 546 A1 | 5/1991 | | |
| EP | 0484546 A1 | * 5/1992 | ............. | B01J 13/06 |

OTHER PUBLICATIONS

M.B. Frish and W.W. Webb, "Direct Measurement of Vorticity by Optical Probe", Journal of Fluid Mechanics 107, 173-200 (1981).
(Continued)

*Primary Examiner* — Jeffrey D Washville
(74) *Attorney, Agent, or Firm* — Thomas | Horstemeyer, LLP

(57) ABSTRACT

Spherical microcapsules including light reflecting solid integral particles reflecting incoming light in a defined direction for determining the position and orientation of the microcapsule are produced by preparing a first liquid phase containing a first polymerization partner; preparing a second liquid phase containing a second polymerization partner, the first liquid phase not being soluble in the second liquid phase, and the second polymerization partner being configured to polymerize with the first polymerization partner under polymerization conditions; dispersing the solid particles in the first liquid phase; forming droplets of the first liquid phase including at least one solid particle; and
(Continued)

immersing the droplets in the second liquid phase under the polymerization conditions. The first polymerization partner and the second polymerization partner polymerize at the surfaces of the droplets forming shells of a polymeric material enclosing the individual droplets, and the light reflecting solid integral particles are fixed to the shells.

20 Claims, 4 Drawing Sheets

(51) Int. Cl.
*G01N 21/53* (2006.01)
*C08G 18/76* (2006.01)
*C08G 18/64* (2006.01)
*C08K 3/22* (2006.01)
*C08K 3/36* (2006.01)

(52) U.S. Cl.
CPC ............... *C08K 3/36* (2013.01); *C08K 9/02* (2013.01); *G01N 21/53* (2013.01); *C08K 2003/2241* (2013.01)

(56) References Cited

OTHER PUBLICATIONS

Ingmar Polenz et al.: "Controlling the Morphology of Polyurea Microcapsules Using Microfluidics", Langmuir, vol. 30, No. 44, Oct. 16, 2014, pp. 13405-13410.
Jiaxing Huang et al. "Polyanihne nanofibers: facile synthesis and chemical sensors", J. Am. Chem. Soc. 125 (2):314-5, Jan. 2003.
Zhao, Xia and Whitesides "Soft lithographic methods for nanofabrication", J. Am. Chem. 1997, 1069-1074.
Abstract Page from "Simultaneous Velocity and Vorticity Measurement in Turbulence", 66th Annual Meeting of the APS Division of Fluidic Dynamics, vol. 58, No. 18; found at http://adsabs.harvard.edu/abs/2013APS..DFDL14003W.
Wu et al., Direct Vorticity Measurement in Turbulence, 14th European Turbulence Conference, Sep. 1-4, 2013, Lyon, France.
Office Action from the European Patent Office for Applicaiton 15788045.1, dated Mar. 14, 2019.

* cited by examiner

REFLECTING SPHERICAL MICROCAPSULES AND METHODS OF THEIR PRODUCTION

CROSS REFERENCE TO RELATED APPLICATIONS

This application is a continuation of International Application PCT/EP2015/075441 with an International Filing Date of Nov. 2, 2015 and claiming priority to European Patent Application No. 14 191 390.5 entitled "Reflecting Spherical Microcapsules and Methods of their Production", filed on Nov. 1, 2014.

FIELD OF THE INVENTION

The present invention relates to a method of producing spherical microcapsules including light reflecting solid integral particles. Further, the present invention relates to a plurality of such spherical microcapsules for seeding an essentially transparent fluid to track movements of the fluid both in translational and rotational directions.

BACKGROUND OF THE INVENTION

In a conference talk on "Direct Optical Vorticity Probing", 14$^{th}$ European Turbulence Conference, Sep. 1-4, 2013, Lyon, France, the inventors disclosed microcapsules for seeding a liquid fluid to track translational and rotational movements of the fluid. The microcapsules are transparent, neutrally buoyant, spherical, and with a glass mirror encapsulated inside. On average, the microcapsules have a diameter of 70 µm. The refraction index is 1.334, almost the same as the refraction index of water. No further details of the microcapsules, however, were given.

In another talk "Vorticity Measurements in Taylor-Couette Flows" presented on the 66th Annual Meeting of APS DFD, Nov. 24-26, 2013, Pittsburgh, USA, the inventors indicated that the microcapsules comprising the features as indicated above were prepared using a micro-fluidic device in that droplets of a first liquid phase including the micro-sized mirrors are dispensed into a flow of a second liquid phase. No further details were given.

M. B. Frish and W. W. Webb, "Direct Measurement of Vorticity by Optical Probe", Journal of Fluid Mechanics 107, 173-200 (1981) measured the rotation rate of single micro-sized beads to obtain the vorticity of a fluid seeded with the beads. The micro-sized beads were made of a transparent material and encapsulated flat mirror discs.

For the purpose of tracking both translational and rotational movements of a fluid seeded with microcapsules including micro-mirrors, it is important that the microcapsules are small and spherical so that they directly follow the fluid, and that only their micro-mirrors reflect light used for determining the position and orientation of the microcapsules, i.e. that this light is not deflected by the material encapsulating the micro-mirrors.

EP 0 484 546 A1 discloses a microcapsule and a method of making the same. The microcapsule contains core substances enveloped by a capsule film obtained by coagulating fine colloidal particles with an electrolyte. The capsule film is formed, through the use of electrolyte, by coagulating the materials of the film which consist of fine inorganic and/or organic colloidal particles. The method comprises adding a substance to be encapsulated to a dispersion (hydrosol) of fine colloidal particles in which water is used as dispersion medium, dispersing said dispersion in an oil medium to form an emulsion, and coagulating the fine colloidal particles in said emulsion by using an electrolyte. In case the substance to be encapsulated is a water-soluble material, it may simply be mixed in the hydrosol. The substance to be encapsulated may be a dye, pigment, medicine, agricultural chemical, perfume, synthetic material, adhesive, enzyme, bacterial cell, etc.

Ingmar Polenz et al.: "Controlling the Morphology of Polyurea Microcapsules Using Microfluidics", LANGMUIR, vol. 30, no. 44, Oct. 16, 2014, pages 13405-13410 discloses the use of microfluidics to continuously produce mono disperse polyurea microcapsules having either aqueous or non-aqueous cores. The microcapsule shells are formed by the reaction between an isocyanate, dissolved in oil, and an amine, dissolved in water, at the surface of oil-in-water or water-in-oil drops immediately as they are formed. Different microcapsule morphologies can be generated by using this approach. The thickness of the microcapsule shell increases with an increases in the amine solubility in the oil allowing for controlling the shell thickness in a range from tens of nanometers to several micrometers. These microcapsules are provided for applications requiring the encapsulation, delivery, and release of active materials, such as self-healing materials, catalysts, agricultural chemicals, textile chemicals, and chemicals used in paper manufacturing.

US 2012/0129742 A1 discloses microcapsules including a core containing one or more alkali metal borates, optionally hydrated, dispersed in one or more lubricating base oils of mineral, synthetic or natural origin, and a polymer shell.

US 2012/0003285 A1 discloses a method for manufacturing capsule series. The method includes separately conveying a first liquid solution containing a first material and a second liquid solution containing a liquid polyelectrolyte. A series of drops is formed at an outlet, each drop including a central core formed from the first solution and a peripheral film formed from the second solution. Each drop is immersed in a gelling solution containing a reagent capable of reacting with the polyelectrolyte of the film so as to form the gelled casing. The second solution contains at least one surfactant before the former contacts the first solution.

There still is a need of a method of producing spherical microcapsules including light reflecting solid integral particles and a plurality of spherical microcapsules for seeding an essentially transparent fluid to track movements of the fluid both in translational and rotational directions producible by the method, which ensure that the microcapsules follow the flow translation and rotation faithfully and which allow for precisely determining the position and the orientation of the spherical microcapsules using light reflected by their solid integral particles.

SUMMARY OF THE INVENTION

The present invention provides a method of producing spherical microcapsules including light reflecting solid integral particles reflecting incoming light to be reflected by the solid integral particles in a defined direction for determining the position and orientation of the microcapsule. The method comprises the steps of preparing a first liquid phase containing a first polymerization partner; preparing a second liquid phase containing a second polymerization partner, the first liquid phase not being soluble in the second liquid phase, and the second polymerization partner being configured to polymerize with the first polymerization partner under polymerization conditions; dispersing the solid integral particles in the first liquid phase; forming droplets of the first liquid phase including at least one of the solid integral particles; immersing the droplets in the second liquid phase under the polymerization conditions, wherein the first polymerization partner and the second polymerization partner polymerize at the surfaces of the droplets forming shells of a polymeric material enclosing the individual droplets; and fixing the light reflecting solid integral particles to the shells.

Further, the present invention provides a plurality of spherical microcapsules for seeding a transparent fluid to track movements of the fluid both in translational and rotational directions. Each microcapsule comprises a core; a shell of a polymeric material enclosing the core; and at least one light reflecting solid integral particle reflecting incoming light to be reflected by the at least one solid integral particle in a defined direction for determining the position and orientation of the microcapsule, embedded in the core and fixed in its orientation with regard to the shell. The shell and the core are transparent for the light to be reflected by the at least one solid integral particle entering and exiting the microcapsule. The shell is so thin that it does essentially not deflect the light to be reflected by the at least one solid integral particle entering and exiting the microcapsule, and the core includes a main component of the fluid such that a refraction index of the core essentially matches a refraction index of the fluid.

Other features and advantages of the present invention will become apparent to one with skill in the art upon examination of the following drawings and the detailed description. It is intended that all such additional features and advantages be included herein within the scope of the present invention, as defined by the claims.

BRIEF DESCRIPTION OF THE DRAWINGS

The invention can be better understood with reference to the following drawings. The components in the drawings are not necessarily to scale, emphasis instead being placed upon clearly illustrating the principles of the present invention. In the drawings, like reference numerals designate corresponding parts throughout the several views.

DETAILED DESRIPTION

Figure 1:
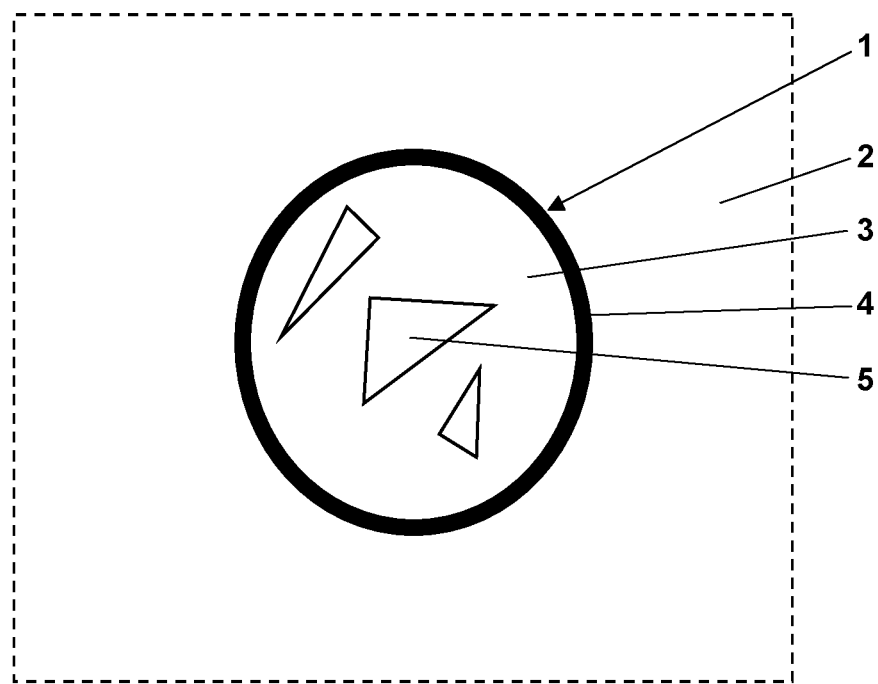
FIG. 1 illustrates a single reflecting spherical microcapsule according to the present invention dispersed in a fluid.

In the method of producing spherical microcapsules including solid integral particles reflecting incoming light to be reflected in a defined direction according to the present invention, a first liquid phase containing a first polymerization partner and a second liquid phase containing a second polymerization partner are prepared. The first and the second liquid phase differ in that at least a base component of the first liquid phase is not soluble in a base component of the second liquid phase. The first and second polymerization partners are selected such that the second polymerization partner polymerizes with the first polymerization partner under polymerization conditions. The term "polymerization partner", however, here also includes a catalyst, i.e. one of the polymerization partners may not become part a polymeric material resulting from the polymerization of the first and second polymerization partners but only catalyze the polymerization of the other polymerization partner. Further, a catalyst may also be present in the first and/or second liquid phase in addition to the first or second polymerization partner, respectively. The solid particles are selected from any light reflecting particles reflecting the incoming light to be reflected in the defined direction for determining the position and orientation of the microcapsule. Particularly, they may be micro-mirrors. They may, however, also be or include diffraction gratings. The solid particles are dispersed in the first liquid phase. From this dispersion of the solid integral particles in the first liquid phase, droplets are formed which include at least one of the solid particles. The formation of the droplets may result in some droplets not including any solid particle which may be discarded or not. The formation of the droplets may further result in droplets including one, two or more solid integral particles which may be separated or not. The droplets are then immersed in the second liquid phase under the polymerization conditions. This results in the first polymerization partner and the second polymerization partner polymerizing at the surfaces of the droplets and thus forming shells of a polymeric material enclosing the individual droplets. A polymerization taking place at an interface of two liquid phases each containing one of the polymerization partners is generally known and called interfacial polymerization. For example, interfacial polymerization is used for producing polyaniline nanofibers, see Jiaxing Huang et al. "Polyaniline nanofibers: facile synthesis and chemical sensors", J. Am. Chem. Soc. 125 (2):314-5, January 2003. In the method of the present invention, the shells formed by interfacial polymerization and enclosing the droplets may be made so thin that they do not deflect light. By appropriately selecting the polymerization partners the shells will nevertheless be durable. The droplets including the solid particles and enclosed by the shells are the desired spherical microcapsules. The spherical shape of the microcapsules may be enhanced by adding a surfactant to the first liquid phase and/or to the second liquid phase.

Preferably, the average number of solid integral particles per microcapsule is between 1 and 5, more preferably, it is between 1 and 3, even more preferably it is between 1 and 2. Typically, the yield of spherical microcapsules including at least one solid integral particle as compared to the entire number of spherical microcapsules produced in the method according o the present invention is 60% to 95%; often it is between 89% and 90%.

The size of the solid integral particles is typically between 5 μm and 100 μm; and often it is between 5 μm and 50 μm, or between a quarter and three quarters of the diameter of the microcapsules.

The light to be reflected may be any light, particularly visible light but also including infrared and ultra-violet light, that is usable in tracking movements of fluids both in translational and rotational directions by being reflected by small particles.

Usually, the microcapsules will not be used as probes for tracking movements of the second liquid phase because the first liquid phase not being soluble in the second liquid phase typically has a quite different refraction index as compared to the second liquid phase. Thus, the method of the present invention will usually further include collecting the droplets enclosed by the shells from the second liquid phase and dispersing the droplets enclosed by the shells in a third liquid phase. The third liquid phase may particularly have a base component identical to the base component of the first liquid phase. If the third liquid phase has a refraction index essentially matching the refraction index of the first liquid phase, the microcapsules are very well suited for tracking translational and rotational movements of the third liquid phase using light reflected by their solid particles, as this light is not deflected at the interface of the microcapsules.

Particularly, the first liquid phase may be soluble in the third liquid phase. Even more particular, the third liquid phase may be water or an aqueous solution, and the first liquid phase may be an aqueous solution including a hydrogel. On the other hand, the second liquid phase may be an oleaginous, i.e. an oil based or oily, phase.

In another embodiment of the method of the present invention, however, the first and third liquid phases may be oleaginous phases whereas the second liquid phase is an aqueous solution. In this embodiment the oleaginous first liquid phase may include a organogel or any other gel entrapping oil.

Examples of suitable organogels include cross-linked polybutadienes, polyacrylates, polystyrenes, polyureas that are formed from formaldehyde derivatives, polyisoprene derivatives (and their cross-linked products using colloidal sulfur) and polysiloxanes. More particular examples of suitable organogeles are disclosed in U.S. Pat. No. 5,298,258 A "Acrylic oily gel bioadhesive material and acrylic oil gel preparation".

In any case, the first liquid phase in the cores of the spherical microcapsules, whose composition differs from that one the polymeric material of the shells may also polymerize or otherwise solidify. Particularly, the first liquid phase may gel or solidify at temperatures below a gelling or solidification temperature. This gelling or solidification temperature may be below a temperature included in the polymerization conditions. Then, the gelling or solidification only takes place after the shells enclosing the droplets are formed when cooling down the microcapsules.

The gelling or solidification of the first liquid phase fixes the solid particles reflecting the light within the microcapsules, i.e. to their shells. This ensures that any translational or rotational movement of the microcapsules is directly transferred onto their light reflecting solid integral particles and may thus be determined using the light reflected by the solid integral particles. If the first liquid phase used for producing the microcapsules does not gel or solidify, it may be necessary to fix the light reflecting particles to the shells of the microcapsules in some other way, like, for example, by polymeric chains.

If the gelling or solidification temperature of the first liquid phase is higher than a use temperature of the microcapsules, which may, for example, be room temperature, the solid integral particles of the microcapsules will always be fixed to their shells when using the microcapsules for probing the vorticity of a fluid, for example.

One of the first and second polymerization partners contained in the first and second liquid phases may be an amine, whereas the other of the first and second polymerization partners may be an isocyanate compound. If the first liquid phase is aqueous solution, whereas the second liquid phase is an oleaginous phase, the amine will be the first polymerization partner in the first liquid phase, whereas the isocyanate compound will be the second polymerization partner in the second liquid phase as the amine is soluble in water whereas the isocyanate is soluble in oil.

In a more particular embodiment of the method of the present invention, the droplets of the first liquid phase including the solid particles are formed by feeding the dispersion of the solid particles in the first liquid phase through an ultrasound spray nozzle into a gaseous phase. Out of the gaseous phase, the droplets may then fall into the second liquid phase. This corresponds to ultrasonic mediated spray deposition of the droplets through the gaseous phase into the second liquid phase.

In another more particular embodiment of the method of the present invention, the droplets are formed of the first liquid phase including the solid particles and immersed in the second liquid phase within a micro-fluidic device. A clog-free production of the microcapsules is achieved in that the first liquid phase is first fed into a flow of a fourth liquid phase not yet including the second polymerization partner to form the droplets, before adding the second polymerization partner to prepare the second liquid phase including the fourth liquid phase. Here, the first liquid phase will also not be soluble in the fourth liquid phase, and the second polymerization partner may be added to the fourth liquid phase dissolved in a liquid carrier. The usage of the fourth liquid phase not yet including the second polymerization partner ensures the formulation of separate droplets fully immersed or emulsified in the fourth liquid phase before the polymerization is started by adding the second polymerization partner. This ensures that the polymerization does not result into bonds between individual droplets or between individual droplets and the walls of the microfluidic device clogging the microfluidic device.

Both more particular embodiment of the method of the present invention may be used to produce monodisperse microcapsules, i.e. a plurality microcapsules of a same diameter. Such monodisperse microcapsules have identical flow properties, i.e. they follow a flow of a fluid seeded with the microcapsules in an identical way.

In a plurality of spherical microcapsules for seeding an essentially transparent fluid to track movements of the fluid both in translational and rotational directions according to the present invention, each microcapsule comprises a core, a shell of a polymeric material enclosing the core, and at least one light reflecting solid integral particle reflecting incoming light to be reflected in a defined direction for determining the position and orientation of the microcapsule, embedded in the core and fixed to the shell. The shell and the core are essentially transparent for light to be reflected by the at least one solid integral particle and the light reflected by the at least one solid integral particle used for determining the position and orientation of the individual microcapsule, i.e. for the light entering and exiting the microcapsule. This is achieved in that the shell is so thin that it does essentially not deflect the light entering and exiting the microcapsule, and in that the core includes a main component of the fluid such that a refraction index of the core essentially matches a refraction index of the fluid. Essentially matching refraction indices may differ by a few percent. Due to the small diameter of the microspheres, these small differences in refraction index will not result in a relevant defection of the light entering and exiting the microcapsules.

In the terms "essentially transparent" and "does essentially not deflect", the word "essentially", is used to indicate that the light is predominantly transmitted or not deflected, respectively. For example, the intensity of the light to be reflected may be reduced by up to about 40%. Preferably, however, it is not reduced by more than 20%, more preferably it is not reduced by more than 10% and most preferably it is not reduced by more than 5% when passing through one of the spherical microcapsules, either directly or reflected by one of its light reflecting solid integral particles.

In the spherical microcapsules according to the present invention, the shells ensure the structural integrity in that they inhibit that the core dissolves in the fluid seeded with the microcapsules. Further, the polymeric shell ensures the spherical shape of the microcapsules even under shearing forces acting upon the microcapsules. In this regard, they may allow for the main component of the fluid passing the shell and entering into the core to build up some osmotic pressure within the core. The shape of the microcapsules may also be stabilized by gelling or solidification of the core. Gelling or solidification of the core will also fix the solid particle embedded in the core to the shell of the microcapsule.

The polymeric material of the shell will typically have a different refraction index as compared to the fluid and the core of the microcapsules. It will nevertheless not deflect the light to be reflected by the solid integral particle as long as it is not thicker than the wavelength of this light. Preferably, the polymeric material of the shell is even thinner than the wavelength of this light. More preferably, its thickness is not more than half of the wavelength of this light. Most preferably, it is about a quarter of the wavelength of the light. With such a thin shell, the light will not be deflected at the interfaces between the fluid and the shell, and between the shell and the core even with some difference in refraction index between the shell and the core and/or the fluid. In absolute terms, the thickness of the polymeric material of the shell may be in a range from 100 nm to 250 nm.

Preferably, the microcapsules according to the present invention are monodisperse. They will have a minimum diameter of about 10 μm to ensure that the embedded light reflecting solid particles are usable for determining position and orientation of the microcapsules from the light reflected by them. The diameter of the microcapsules may be up to about 200 μm. Preferably, however, it is smaller than 100 μm. Microcapsules having a diameter in a range of 10 μm to 70 μm will perfectly follow most fluids for tracking their vorticity.

Referring now in greater detail to the drawings, FIG. 1 shows a microcapsule 1 dispersed in a fluid 2. The microcapsule consists of a core 3, a shell 4 enclosing the core 3, and a micro-mirror 5 embedded in the core 3. The core 3, besides the micro-mirror 5, consists of a hydrogel that is gelled at a use temperature of the microcapsule 1. The hydrogel consists of a polymeric component and water. The gelled hydrogel fixes the orientation of the micro-mirror 5 in the microcapsule 1, i.e. every movement of the shell 4 due to any translational or rotational movement of the fluid 2 is transferred to the micro-mirror 5. The micro-mirror 5 is provided in the microcapsule 1 to reflect light and to allow for determining the position and orientation of the microcapsule 1 within the fluid 2 due to the direction into which the light coming out of defined direction is reflected. To not disturb this determination of the position and orientation of the microcapsule 1 by any deflection of the light, a refraction index of the core 3, i.e. of the hydrogel, matches a refraction index of the fluid 2 which is an aqueous solution, i.e. which has the same base component water as the core 3. The shell 4 does not deflect the light, because its thickness is only about a quarter of a wavelength of the light. As a result, the shell 4 is basically invisible to the light. It is to be understood that the fluid 2, the shell 4 and the core 3 have to be transparent to determine the position and orientation of the microcapsule due to light reflected by the micro-mirror 5 and that the micro-mirror 5 has to be plane. Instead of a plane micro-mirror 5, however, another solid particle reflecting incoming light in a defined direction could be embedded in the core 3. This other particle could, for example, be a diffraction grating. The shell 4 is made of a polymeric material through which water may pass to a limited extent like through a semipermeable membrane. The amount of water which may pass through the shell 4 will, however, be limited by the resulting osmotic pressure in the core 3. For example, the shell 4 may consist of an isocyanate-based polymer which is of high toughness and elasticity even at the low thickness. Particularly, this thickness may be in the order of several ten nanometers, i.e. of less than half the wavelength of visible light. The actual thickness of the shell 4 may be adjusted by appropriately selecting its components and the conditions under which the microcapsule 1 is produced of the shell 4. Instead of a hydrogel in the core 3 and an aqueous solution or water as the fluid 2, both the core 3 and the fluid 2 may comprise an oil as their base component. In this case, the refraction index of the core 3 is also matched to the refraction index of the fluid 2.

In another embodiment of the microcapsule 1, the core 3, besides the micro-mirror 5, consists of an organogel entrapping a oleaginous liquid phase and gelled at the use temperature of the microcapsule 1. Here, the gelled organogel fixes the orientation of the micro-mirror 5 in the microcapsule 1, and a refraction index of the core 3, i.e. of the organogel, matches a refraction index of the fluid 2 which is an oleaginous solution, i.e. which has the same oily base component as the core 3.

Figure 2:
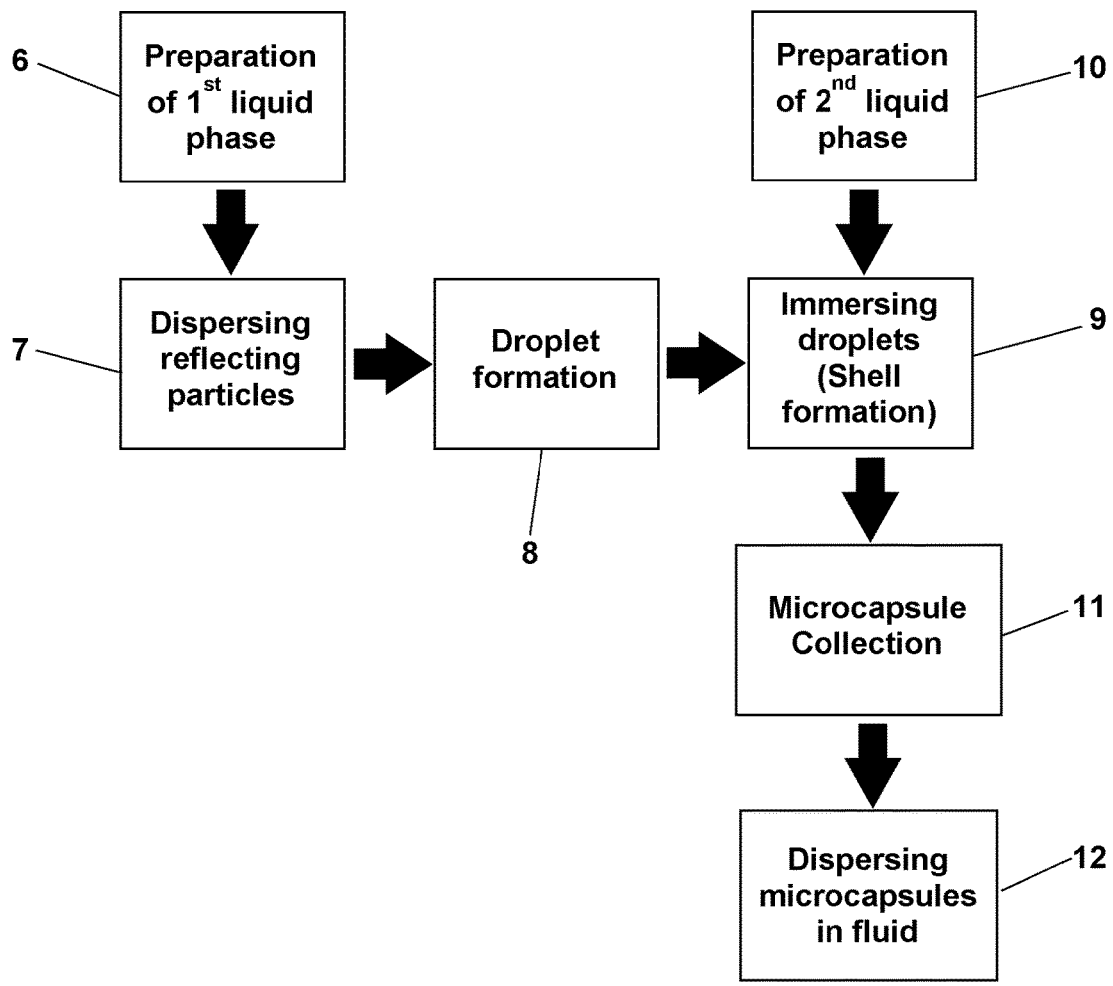
FIG. 2 is a block diagram illustrating the steps of the method of producing microcapsules according to the present invention.

According to the present invention, the microcapsule 1 according to FIG. 1 is prepared as illustrated in FIG. 2. In step 6, a first liquid phase is prepared. This liquid phase will later form the core 3 of the microcapsule 1. Further, it includes a first polymerization partner soluble in the liquid phase. In step 7, reflecting particles like the micro-mirror 5 are dispersed in the first liquid phase. In step 8, droplets are formed of the dispersion formed in step 7 with the aim to include at least one reflecting particle in each droplet. In step 9, these droplets are immersed in a second liquid phase which is prepared in step 10. The second liquid phase contains a second polymerization partner which, upon immersing the droplets in the second liquid phase, together with the first polymerization partner contained in the first liquid phase forms the shell 4 of the microcapsule 1 by interfacial polymerization. The first liquid phase is not soluble in the second liquid phase. Instead, it is preferred to have a considerable interfacial surface tension ensuring a spherical shape of the microcapsules. As a result, however, there will be a considerable difference in refraction indices between the first and second liquid phases, i.e. the second liquid phase may not be the fluid 2 according to FIG. 1. Therefore, in step 11, the microcapsules are collected or separated from the second liquid phase, and in step 12 they are dispersed in the fluid 2 or a liquid of similar composition.

Figure 3:
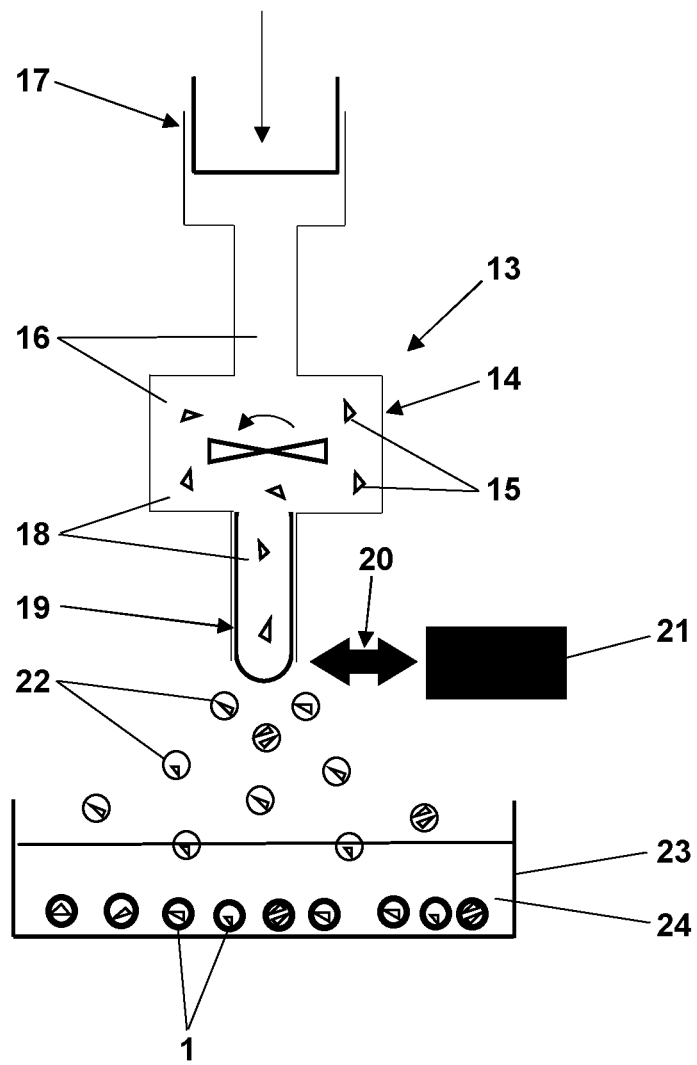
FIG. 3 illustrates an ultrasound spray device for producing the microcapsules according to the present invention.

FIG. 3 illustrates an ultrasonic spray deposition device 13 for producing the microcapsules 1 according to the present invention. In a mixing container 14 the light reflecting particles 15 are dispersed in the first liquid phase 16. A syringe-styled pump 17 feeds the dispersion 18 formed in the mixing container 14 to a spray nozzle 19 subject to ultrasound 20 generated by an ultrasound generator 21. The dispersion 18 exiting the spray nozzle 19 is disrupted into the droplets 22 which fall into a basin 23 containing the second liquid phase 24. As soon as the droplets 22 are immersed in the second liquid phase 24, the microcapsules 1 are formed. With appropriately selected components and conditions of production, the microcapsules will directly be monodisperse, or they will be of such different diameter, because the bigger microspheres are due to an agglomeration of two or more initial droplets 22, that a monodisperse plurality of microcapsules may easily be separated. This first liquid phase may only be liquid when heated up to a temperature above room temperature so that the core 3 of the microcapsules 1 gels or solidifies when getting down to room temperature. The microcapsules 1 produced by the ultrasonic spray deposition device 13 according to FIG. 3 have a typical diameter of 15-60 µm with an average size of about 40 µm. The first polymerization partner contained in the first liquid phase 16 may be an amine, whereas the second polymerization partner included in the second liquid phase 24 may be an isocyanate compound, i.e. a very reactive polymerization partner which quickly reacts with the amine in the first liquid phase 16 to form the shells 4 of a polymeric material by interfacial polymerization.

Figure 4:
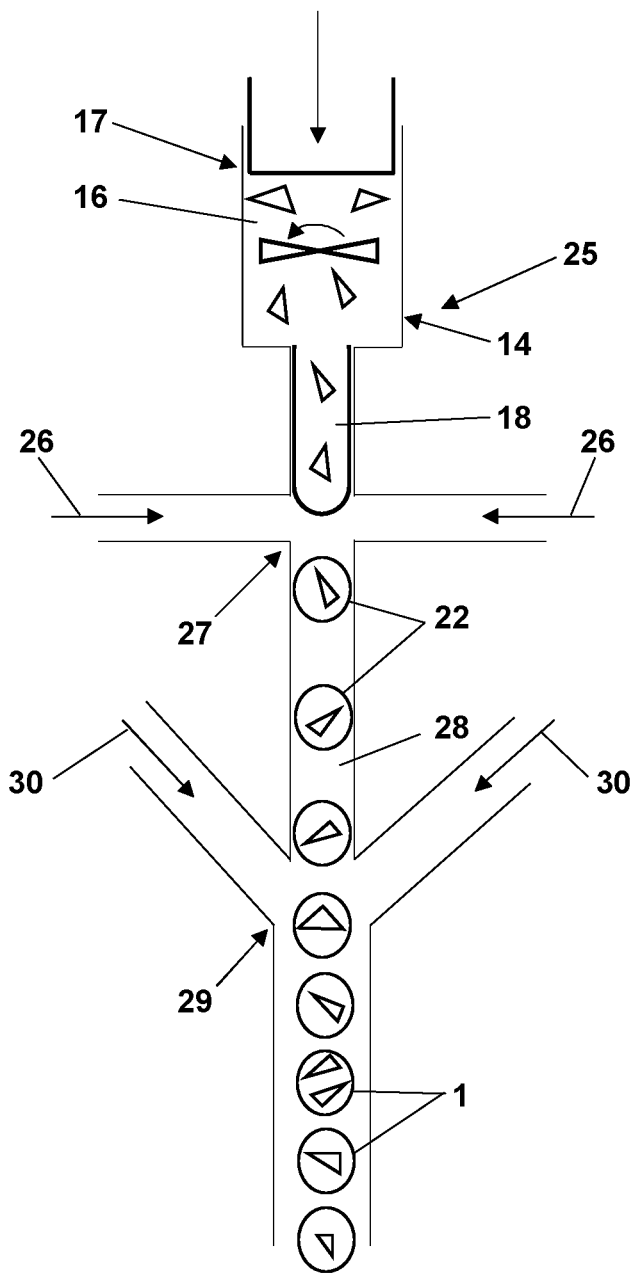
FIG. 4 illustrates a microfluidic device for producing the microcapsules according to the present invention.

FIG. 4 depicts a microfluidic device 25 which may alternatively be used for producing the microcapsules according to the present invention. The microfluidic device 25 may, for example, be fabricated by standard methods using soft lithography, see for example Y. N. Xia, G. M. Whitesides, *Abstr. Pap. Am. Chem. Soc.* 1997, 214, 348. In one example of using the microfluidic device 25 for producing the microcapsules according to the present invention, the first liquid phase 16 is a 5% by weight gelatin solution (Bovine Skin, Sigma Aldrich) supplemented with 0.5% by weight polyethyleneimine (PEI, Sigma Aldrich) as the first polymerization partner. In this first liquid phase 16, 0.5% by weight glitter flakes (Ho Long Glitter Enterprises Co., average size 20 µm) are dispersed as micro-mirrors. The resulting dispersion 18 is dispersed in an oleaginous solution 26 consisting of kmc oil (isomer mixture of disopropylnaphthalene). By means of homogeneous shearing at a T-junction 27 of the microfluidic device 25, a continuous rip-off of droplets 22 is achieved resulting in the production of a monodisperse droplet emulsion 28. The emulsion 28 flows into a V-junction 29 where a further oleaginous solution 30 composed of 0.1% by weight Pluronics P123 (Sigma Aldrich) and 5% by weight 2.4-toluene diisocyanate (TDI, Sigma Aldrich) that are dissolved in kmc oil is fed. In combination, the oleaginous solutions 26 and 30 form the second liquid phase 24. After the V-junction 29, the TDI in the second liquid phase 24 reacts with the PEI to form the shells enclosing the droplets 22 to form monodisperse microcapsules 1. The microcapsules 1 are then purified and transferred into an aqueous phase by decanting the capsules with tetrahydrofuran (THF) for several times to get rid of residual surfactant (P123) and unreacted TDI, and transferring the highly concentrated suspension into an aqueous surfactant (P123) solution. Under these conditions the microcapsules are longtime stable for several months. The details of the compositions of the materials and the figures indicated here allow for working the present invention. They are, however, not critical to the present invention.

Both the ultrasonic method illustrated in FIG. 2 and the microfluidic method illustrated in FIG. 4 produce spherical microcapsules including light reflecting solid integral particles according to the present invention. In an example of the ultrasonic method, 89% of the produced spherical microcapsules included at least one light reflecting solid integral particle, and the average number of light reflecting solid integral particles per spherical microcapsule was 1.6. In an example of the microfluidic method, 81% of the produced spherical microcapsules included at least one light reflecting solid integral particle, and the average number of light reflecting solid integral particles per spherical microcapsule was 3.3.

An example of the light reflecting particles to be used in the spherical microcapsules are $TiO_2$ coated $SiO_2$ snippets of irregular shape that are commonly used in decoration industry and in care materials. A typical particle size distribution of the light reflecting particles used within the above examples extends from above 5 µm to about 40 µm, the maximum dimension of most of the particles being smaller than 20 µm with.

The shell thicknesses of the spherical microcapsules produced were in a typical range of 100 nm to 250 nm.

With a concentration of the gelatin in the spherical microcapsules increasing from 2.5% to 10% by weight, their transparency for visible light provided by a halogen lamp dropped from 96% to 59% with still being at 86% with 5% by weight gelatin. The transparency was determined from an average brightness of bright light microscopic images of several spherical microcapsules taken with a digital camera sensitive for visible light as compared to the background brightness of the images.

Many variations and modifications may be made to the preferred embodiments of the invention without departing substantially from the spirit and principles of the invention. All such modifications and variations are intended to be included herein within the scope of the present invention, as defined by the following claims.

We claim:

1. A method of producing monodisperse spherical microcapsules comprising a shell and a core, the method comprising:
    preparing a first liquid phase containing a first polymerization partner;
    preparing a second liquid phase containing a second polymerization partner, the first liquid phase not being soluble in the second liquid phase, and the second polymerization partner being configured to polymerize with the first polymerization partner under interfacial polymerization conditions;
    dispersing light reflecting solid integral particles in the first liquid phase;
    forming droplets of the first liquid phase including at least one of the light reflecting solid integral particles;
    immersing the droplets in the second liquid phase under the interfacial polymerization conditions, wherein the first polymerization partner and the second polymerization partner polymerize at the surfaces of the droplets forming shells of a polymeric material enclosing the individual droplets; and
    fixing the light reflecting solid integral particles to the shells;
    thereby producing monodisperse spherical microcapsules comprising the core and the shell;
    wherein the core comprises 1 to 5 light reflecting solid integral particles per microcapsule; and
    wherein the shell comprises the polymeric material.

2. The method of claim 1, further comprising collecting the droplets enclosed by the shells from the second liquid phase and dispersing the droplets enclosed by the shells in a third liquid phase, the third liquid phase having a refraction index essentially matching a refraction index of the first liquid phase.

3. The method of claim 2, wherein the first liquid phase is soluble in the third liquid phase.

4. The method of claim 2, wherein the third liquid phase is water or an aqueous solution.

5. The method of claim 1, wherein one of the first and second liquid phases is an aqueous phase, whereas the other of the first and second liquid phases is an oleaginous phase.

6. The method of claim 1, wherein the first liquid phase is an aqueous solution including a hydrogel, or an oleaginous solution including an organogel.

7. The method of claim 1, wherein the first liquid phase gels or solidifies at temperatures below a gelling or solidification temperature, the polymerization conditions including a temperature above the gelling or solidification temperature.

8. The method of claim 7, wherein the gelling or solidification temperature is higher than a use temperature of the microcapsules.

9. The method of claim 1, wherein first liquid phase or the gelled or solidified first liquid phase is transparent for the light to be reflected by the light reflecting solid integral particles.

10. The method of claim 1, wherein one of the first and second polymerization partners is an amine, and the other of the first and second polymerization partners is an isocyanate compound.

11. The method of claim 1, wherein the droplets are formed by feeding the first liquid phase including the light reflecting solid integral particles through a spray nozzle into a gaseous phase.

12. The method of claim 1, wherein the droplets are formed of the first liquid phase including the light reflecting solid integral particles and immersed in the second liquid phase in a microfluidic device, wherein the first liquid phase including the solid parts is fed into a flow of a fourth liquid phase not including the second polymerization partner before adding the second polymerization partner to prepare the second liquid phase including the fourth liquid phase.

13. The method of claim 1, wherein the shell has a thickness of not more than $\lambda$; and wherein $\lambda$ is a wavelength of light to be reflected by the light reflecting solid integral particles.

14. The method of claim 1, wherein the monodisperse spherical microcapsules have a diameter in a range of 10 μm to 200 μm.

15. A plurality of monodisperse spherical microcapsules made by the method of claim 1, wherein each monodisperse spherical microcapsule comprises:
   a core;
   a shell of a polymeric material enclosing the core; and
   at least one light reflecting solid integral particle reflecting incoming light to be reflected by the at least one solid integral particle in a defined direction for determining the position and orientation of the microcapsule, embedded in the core and fixed in its orientation with regard to the shell;
   wherein the shell and the core are transparent for the light to be reflected by the at least one light reflecting solid integral particle entering and exiting the microcapsule,
   wherein the shell is so thin that it does essentially not deflect the light to be reflected by the at least one light reflecting solid integral particle entering and exiting the microcapsule, and
   wherein the core includes a main component of the transparent fluid such that a refraction index of the core essentially matches a refraction index of the transparent fluid.

16. The plurality of monodisperse spherical microcapsules of claim 15, wherein the shell has a thickness of not more than $\lambda$; and wherein $\lambda$ is a wavelength of light to be reflected by the at least one solid integral particle.

17. The plurality of monodisperse spherical microcapsules of claim 15, wherein the microcapsules have a diameter in a range of 10 μm to 200 μm.

18. The method of claim 1, wherein the monodisperse spherical microcapsules have a diameter in a range of 10 μm to 70 μm.

19. The method of claim 13, wherein the shell has a thickness of not more than $\lambda/2$.

20. The plurality of monodisperse spherical microcapsules of claim 16, wherein the shell has a thickness of not more than $\lambda/2$.

* * * * *